US011953651B2

(12) United States Patent
McCabe et al.

(10) Patent No.: US 11,953,651 B2
(45) Date of Patent: *Apr. 9, 2024

(54) COMFORTABLE OPHTHALMIC DEVICE AND METHODS OF ITS PRODUCTION

(71) Applicant: Johnson & Johnson Vision Care, Inc., Jacksonville, FL (US)

(72) Inventors: Kevin P. McCabe, St. Augustine, FL (US); Robert B. Steffen, Webster, NY (US); Hélène Aguilar, St. Augustine Beach, FL (US); W. Anthony Martin, Orange Park, FL (US); Susan W. Neadle, Jacksonville, FL (US); Ann-Marie Wong Meyers, Jacksonville, FL (US); Douglas G. Vanderlaan, Jacksonville, FL (US); Dominic P. Gourd, Ponte Vedra Beach, FL (US); Kristy L. Canavan, Jacksonville, FL (US); Gregory A. Hill, Pleasant Valley, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 81 days.

This patent is subject to a terminal disclaimer.

(21) Appl. No.: 17/410,139

(22) Filed: Aug. 24, 2021

(65) Prior Publication Data
US 2022/0206187 A1 Jun. 30, 2022

Related U.S. Application Data

(60) Continuation of application No. 16/293,819, filed on Mar. 6, 2019, now Pat. No. 11,150,383, which is a
(Continued)

(51) Int. Cl.
G02B 1/04 (2006.01)
A61L 12/04 (2006.01)
(Continued)

(52) U.S. Cl.
CPC .............. *G02B 1/043* (2013.01); *A61L 12/04* (2013.01); *A61L 12/08* (2013.01); *A61L 27/34* (2013.01);
(Continued)

(58) Field of Classification Search
None
See application file for complete search history.

(56) References Cited

U.S. PATENT DOCUMENTS 2,847,407 A 8/1958 Hosmer
3,311,577 A 3/1967 Rankin
(Continued)

FOREIGN PATENT DOCUMENTS

CN 1074450 A 7/1993
CN 1230882 A 10/1999
(Continued)

OTHER PUBLICATIONS

Aquavella et al, Therapeutic Effects of Bionite Lenses: Mechanisms of Action, Annals of Ophthalmology (12):1341-1345, 1971, 10 pages.
(Continued)

Primary Examiner — Eric W Golightly
(74) Attorney, Agent, or Firm — Raef M. Shaltout

(57) ABSTRACT

This invention relates to comfortable ophthalmic devices and methods of producing such devices.

6 Claims, 1 Drawing Sheet

Related U.S. Application Data continuation of application No. 15/175,526, filed on Jun. 7, 2016, now Pat. No. 10,267,952, which is a division of application No. 14/196,006, filed on Mar. 4, 2014, now Pat. No. 9,395,559, which is a division of application No. 12/896,930, filed on Oct. 4, 2010, now Pat. No. 8,696,115, which is a continuation of application No. 11/351,907, filed on Feb. 10, 2006, now Pat. No. 7,841,716.

(60) Provisional application No. 60/695,783, filed on Jun. 30, 2005, provisional application No. 60/652,809, filed on Feb. 14, 2005.

(51) Int. Cl.
    *A61L 12/08*      (2006.01)
    *A61L 27/34*      (2006.01)
    *A61L 27/50*      (2006.01)
    *A61L 27/54*      (2006.01)
    *B29D 11/00*      (2006.01)
    *G02C 7/04*      (2006.01)
    *G02C 13/00*      (2006.01)

(52) U.S. Cl.
    CPC .............. *A61L 27/50* (2013.01); *A61L 27/54* (2013.01); *B29D 11/00067* (2013.01); *G02C 7/049* (2013.01); *G02C 13/00* (2013.01); *A61L 2300/452* (2013.01); *B29K 2039/06* (2013.01)

(56) References Cited

U.S. PATENT DOCUMENTS

| | | |
|---|---|---|
| 3,408,429 A | 10/1968 | Wichterle |
| 3,621,079 A | 11/1971 | Leeds |
| 3,660,545 A | 5/1972 | Wichterle |
| 3,700,761 A | 10/1972 | O'Driscoll et al. |
| 3,721,657 A | 3/1973 | Seiderman |
| 3,767,731 A | 10/1973 | Seiderman |
| 3,767,788 A | 10/1973 | Rankin |
| 3,808,178 A | 4/1974 | Gaylord |
| 3,841,598 A | 10/1974 | Grucza |
| 3,841,965 A | 10/1974 | O'Driscoll et al. |
| 3,888,782 A | 6/1975 | Boghosian et al. |
| 3,894,129 A | 7/1975 | Hoffman et al. |
| 3,910,761 A | 10/1975 | Hopkins |
| 3,947,573 A | 3/1976 | Rankin |
| 3,954,644 A | 5/1976 | Krezanoski et al. |
| 3,959,102 A | 5/1976 | Wajs et al. |
| 3,966,847 A | 6/1976 | Seiderman |
| 3,978,164 A | 8/1976 | Le Boeuf et al. |
| 4,018,853 A | 4/1977 | Le Boeuf et al. |
| RE29,231 E | 5/1977 | Leeds |
| 4,029,817 A | 6/1977 | Blanco et al. |
| 4,038,264 A | 7/1977 | Rostoker et al. |
| 4,042,552 A | 8/1977 | Grucza |
| 4,045,547 A | 8/1977 | Le Boeuf et al. |
| 4,054,624 A | 10/1977 | Le Boeuf et al. |
| 4,062,627 A | 12/1977 | Wajs et al. |
| 4,113,224 A | 9/1978 | Clark et al. |
| 4,120,570 A | 10/1978 | Gaylord |
| 4,123,408 A | 10/1978 | Gordon |
| 4,136,250 A | 1/1979 | Mueller et al. |
| 4,153,641 A | 5/1979 | Deichert et al. |
| 4,157,892 A | 6/1979 | Tanaka et al. |
| 4,190,277 A | 2/1980 | England |
| 4,197,266 A | 4/1980 | Clark et al. |
| 4,321,261 A | 3/1982 | Ellis et al. |
| 4,407,791 A | 10/1983 | Stark |
| 4,451,629 A | 5/1984 | Tanaka et al. |
| 4,460,573 A | 7/1984 | Huth et al. |
| 4,495,313 A | 1/1985 | Larsen |
| 4,525,346 A | 6/1985 | Stark |
| 4,529,535 A | 7/1985 | Sherman |
| 4,560,491 A | 12/1985 | Sherman |
| 4,615,882 A | 10/1986 | Stockel |
| 4,626,292 A | 12/1986 | Sherman |
| 4,670,178 A | 6/1987 | Huth et al. |
| 4,680,336 A | 7/1987 | Larsen et al. |
| 4,691,820 A | 9/1987 | Martinez |
| 4,729,914 A | 3/1988 | Kliment et al. |
| 4,731,192 A | 3/1988 | Kenjo et al. |
| 4,740,533 A | 4/1988 | Su et al. |
| 4,866,148 A | 9/1989 | Geyer et al. |
| 4,889,664 A | 12/1989 | Kindt-Larsen et al. |
| 4,910,277 A | 3/1990 | Bambury et al. |
| 4,961,954 A | 10/1990 | Goldberg et al. |
| 4,976,969 A | 12/1990 | Plamondon |
| 5,001,009 A | 3/1991 | Whitbourne |
| 5,006,622 A | 4/1991 | Kunzler et al. |
| 5,034,461 A | 7/1991 | Lai et al. |
| 5,039,459 A | 8/1991 | Kindt-Larsen et al. |
| 5,057,578 A | 10/1991 | Spinelli |
| 5,070,170 A | 12/1991 | Robertson et al. |
| 5,070,215 A | 12/1991 | Bambury et al. |
| 5,094,876 A | 3/1992 | Goldberg et al. |
| 5,100,689 A | 3/1992 | Goldberg et al. |
| 5,117,165 A | 5/1992 | Cassat et al. |
| 5,130,124 A | 7/1992 | Merianos et al. |
| 5,135,297 A | 8/1992 | Valint, Jr. |
| 5,141,665 A | 8/1992 | Sherman |
| 5,244,981 A | 9/1993 | Seidner et al. |
| 5,256,751 A | 10/1993 | Vanderlaan |
| 5,300,296 A | 4/1994 | Holly et al. |
| 5,311,223 A | 5/1994 | Vanderlaan |
| 5,312,588 A | 5/1994 | Gyulai et al. |
| 5,314,960 A | 5/1994 | Spinelli et al. |
| 5,314,961 A | 5/1994 | Anton et al. |
| 5,321,108 A | 6/1994 | Kunzler et al. |
| 5,322,667 A | 6/1994 | Sherman |
| 5,331,067 A | 7/1994 | Seidner et al. |
| 5,338,480 A | 8/1994 | Dziabo et al. |
| 5,338,814 A | 8/1994 | Wu et al. |
| 5,356,555 A | 10/1994 | Huth et al. |
| 5,358,995 A | 10/1994 | Lai et al. |
| 5,362,815 A | 11/1994 | Shih et al. |
| 5,364,918 A | 11/1994 | Valint, Jr. et al. |
| 5,373,074 A | 12/1994 | Wu et al. |
| 5,380,303 A | 1/1995 | Holly et al. |
| 5,387,662 A | 2/1995 | Kunzler et al. |
| 5,436,068 A | 7/1995 | Kobayashi et al. |
| 5,443,801 A | 8/1995 | Langford |
| 5,451,303 A | 9/1995 | Heiler et al. |
| 5,466,853 A | 11/1995 | Koinuma et al. |
| 5,467,868 A | 11/1995 | Abrams et al. |
| 5,486,579 A | 1/1996 | Lai et al. |
| 5,488,815 A | 2/1996 | Abrams et al. |
| 5,496,871 A | 3/1996 | Lai et al. |
| 5,525,691 A | 6/1996 | Valint, Jr. et al. |
| 5,539,016 A | 7/1996 | Kunzler et al. |
| 5,577,367 A | 11/1996 | Abrams et al. |
| 5,585,186 A | 12/1996 | Scholz et al. |
| 5,603,897 A | 2/1997 | Heiler et al. |
| 5,641,450 A | 6/1997 | Kobayashi et al. |
| 5,652,638 A | 7/1997 | Roffman et al. |
| 5,696,686 A | 12/1997 | Sanka et al. |
| 5,704,468 A | 1/1998 | Lust et al. |
| 5,710,302 A | 1/1998 | Kunzler et al. |
| 5,726,733 A | 3/1998 | Lai et al. |
| 5,743,920 A | 4/1998 | Kohan |
| 5,760,100 A | 6/1998 | Nicolson et al. |
| 5,773,396 A | 6/1998 | Zhang et al. |
| 5,776,999 A | 7/1998 | Nicolson et al. |
| 5,782,992 A | 7/1998 | Frangione |
| 5,789,461 A | 8/1998 | Nicolson et al. |
| 5,800,807 A | 9/1998 | Hu et al. |
| 5,805,260 A | 9/1998 | Roffman et al. |
| 5,807,944 A | 9/1998 | Hirt et al. |
| 5,823,327 A | 10/1998 | Wu et al. |
| 5,840,671 A | 11/1998 | Fujimura et al. |
| 5,849,811 A | 12/1998 | Nicolson et al. |
| 5,873,931 A | 2/1999 | Scholz et al. |
| 5,885,566 A | 3/1999 | Goldberg |

(56) References Cited

U.S. PATENT DOCUMENTS

| | | |
|---|---|---|
| 5,902,606 A | 5/1999 | Wunderlich et al. |
| 5,942,589 A | 8/1999 | Wunsch et al. |
| 5,944,853 A | 8/1999 | Molock et al. |
| 5,965,631 A | 10/1999 | Nicolson et al. |
| 5,998,498 A | 12/1999 | Vanderlaan et al. |
| 6,018,931 A | 2/2000 | Byram et al. |
| 6,039,913 A | 3/2000 | Hirt et al. |
| 6,050,398 A | 4/2000 | Wilde et al. |
| 6,087,415 A | 7/2000 | Vanderlaan et al. |
| 6,093,686 A | 7/2000 | Nakada et al. |
| 6,126,706 A | 10/2000 | Matsumoto et al. |
| 6,162,393 A | 12/2000 | De Bruiju et al. |
| D435,966 S | 1/2001 | Duis et al. |
| 6,180,093 B1 | 1/2001 | De et al. |
| 6,183,082 B1 | 2/2001 | Clutterbuck |
| 6,190,651 B1 | 2/2001 | Nakada et al. |
| 6,258,591 B1 | 7/2001 | Yoneda et al. |
| 6,274,133 B1 | 8/2001 | Hu et al. |
| 6,338,847 B1 | 1/2002 | Thomas |
| 6,367,929 B1 | 4/2002 | Maiden et al. |
| 6,372,815 B1 | 4/2002 | Sulc et al. |
| 6,406,739 B1 | 6/2002 | LeBoeuf et al. |
| 6,428,353 B2 | 8/2002 | Mochizuki |
| 6,440,366 B1 | 8/2002 | Salpekar et al. |
| 6,444,776 B1 | 9/2002 | Holland et al. |
| 6,488,965 B1 | 12/2002 | Karageozian |
| 6,511,949 B1 | 1/2003 | Nitta et al. |
| 6,528,048 B1 | 3/2003 | Koike et al. |
| 6,565,776 B1 | 5/2003 | Li et al. |
| 6,617,373 B2 | 9/2003 | Sulc et al. |
| 6,699,435 B2 | 3/2004 | Salpekar et al. |
| 6,733,123 B2 | 5/2004 | Polzhofer et al. |
| 6,815,074 B2 | 11/2004 | Aguado et al. |
| 6,822,016 B2 | 11/2004 | McCabe et al. |
| 6,849,671 B2 | 2/2005 | Steffen et al. |
| 6,861,123 B2 | 3/2005 | Turner et al. |
| 6,867,172 B2 | 3/2005 | Alvarez et al. |
| 6,940,580 B2 | 9/2005 | Winterton et al. |
| 6,992,118 B2 | 1/2006 | Sulc et al. |
| 7,052,131 B2 | 5/2006 | McCabe et al. |
| 7,143,990 B2 | 12/2006 | Matsuzawa et al. |
| 7,147,844 B2 | 12/2006 | Hamano et al. |
| 7,262,232 B2 | 8/2007 | Sulc et al. |
| 7,431,152 B2 | 10/2008 | Marmo |
| 7,435,452 B2 | 10/2008 | Shimoyama et al. |
| 7,841,716 B2 | 11/2010 | McCabe et al. |
| 8,672,475 B2 | 3/2014 | Liu et al. |
| 8,696,115 B2 | 4/2014 | McCabe et al. |
| 9,052,529 B2 | 6/2015 | McCabe et al. |
| 9,395,559 B2 * | 7/2016 | McCabe ............... G02B 1/043 |
| 11,150,383 B2 | 10/2021 | McCabe et al. |
| 2001/0036556 A1 | 11/2001 | Jen |
| 2001/0044482 A1 | 11/2001 | Hu et al. |
| 2002/0039984 A1 | 4/2002 | Ketelson et al. |
| 2002/0058601 A1 | 5/2002 | Jordan, IV et al. |
| 2003/0044447 A1 | 3/2003 | Zanini et al. |
| 2003/0109390 A1 | 6/2003 | Salpekar et al. |
| 2003/0164562 A1 | 9/2003 | Li et al. |
| 2003/0191043 A1 | 10/2003 | Becker et al. |
| 2004/0091613 A1 | 5/2004 | Wood et al. |
| 2004/0097504 A1 | 5/2004 | Bethiel et al. |
| 2004/0114105 A1 | 6/2004 | Shimoyama et al. |
| 2004/0120982 A1 | 6/2004 | Diana et al. |
| 2004/0130676 A1 | 7/2004 | Doshi et al. |
| 2004/0137079 A1 | 7/2004 | Cook et al. |
| 2004/0142829 A1 | 7/2004 | Tsao et al. |
| 2004/0150788 A1 | 8/2004 | Andersson et al. |
| 2004/0186028 A1 | 9/2004 | Hu et al. |
| 2004/0192872 A1 | 9/2004 | Iwata et al. |
| 2004/0214914 A1 | 10/2004 | Marmo |
| 2005/0059639 A1 | 3/2005 | Wei |
| 2005/0074467 A1 | 4/2005 | Fujita et al. |
| 2005/0117112 A1 | 6/2005 | Nayiby et al. |
| 2005/0154080 A1 | 7/2005 | McCabe et al. |
| 2005/0179862 A1 | 8/2005 | Steffen et al. |
| 2007/0010595 A1 | 1/2007 | McCabe et al. |
| 2007/0043140 A1 | 2/2007 | Lorenz et al. |
| 2007/0119721 A1 | 5/2007 | Marmo |
| 2007/0229758 A1 | 10/2007 | Matsuzawa |
| 2008/0045612 A1 | 2/2008 | Rathore et al. |
| 2008/0100796 A1 | 5/2008 | Pruitt et al. |
| 2008/0141628 A1 | 6/2008 | Lang et al. |
| 2008/0148689 A1 | 6/2008 | Xia et al. |
| 2008/0299179 A1 | 12/2008 | Rathore et al. |
| 2008/0307751 A1 | 12/2008 | Newman et al. |
| 2009/0059165 A1 | 3/2009 | Pruitt et al. |
| 2009/0182067 A1 | 7/2009 | Liu |
| 2010/0162663 A1 | 7/2010 | McGee et al. |
| 2010/0238399 A1 | 9/2010 | Rathore |
| 2011/0262519 A1 | 10/2011 | Franklin et al. |
| 2012/0026457 A1 | 2/2012 | Qiu et al. |
| 2013/0293831 A1 | 11/2013 | Norris et al. |
| 2014/0016086 A1 | 1/2014 | Liu et al. |

FOREIGN PATENT DOCUMENTS

| | | |
|---|---|---|
| EP | 0080539 B1 | 6/1983 |
| EP | 349487 A2 | 1/1990 |
| EP | 358447 A2 | 3/1990 |
| EP | 472496 A2 | 2/1992 |
| EP | 487994 A1 | 6/1992 |
| EP | 0406161 B1 | 2/1995 |
| EP | 482836 B1 | 3/1995 |
| EP | 482837 B1 | 3/1995 |
| EP | 486653 B1 | 5/1996 |
| EP | 600828 B1 | 3/1997 |
| EP | 437179 B1 | 4/1998 |
| EP | 836111 A1 | 4/1998 |
| EP | 580662 B1 | 6/1998 |
| EP | 577143 B1 | 1/1999 |
| EP | 456467 B1 | 4/1999 |
| EP | 650354 B1 | 12/1999 |
| EP | 979659 B1 | 2/2005 |
| EP | 1327893 B1 | 7/2006 |
| GB | 1212758 A | 11/1970 |
| JP | 58216222 | 12/1983 |
| JP | S58216222 A | 12/1983 |
| JP | H0259346 A | 2/1990 |
| JP | 199086643 | 3/1990 |
| JP | H0286643 A | 3/1990 |
| JP | 4370197 | 12/1992 |
| JP | H04370197 A | 12/1992 |
| JP | 1993173098 | 7/1993 |
| JP | H05173098 A | 7/1993 |
| JP | 1994312013 | 11/1994 |
| JP | H0730247 A | 1/1995 |
| JP | 8500382 | 1/1996 |
| JP | 1996196270 | 8/1996 |
| JP | H0925679 A | 1/1997 |
| JP | 10114807 | 5/1998 |
| JP | 1998221654 | 8/1998 |
| JP | H10218991 A | 8/1998 |
| JP | H1143554 A | 2/1999 |
| JP | 2899347 B2 | 6/1999 |
| JP | H11161298 A | 6/1999 |
| JP | H11161299 A | 6/1999 |
| JP | 2000016905 | 1/2000 |
| JP | 2000056277 | 2/2000 |
| JP | 2000239696 | 9/2000 |
| JP | 2000347145 | 12/2000 |
| JP | 2000347146 | 12/2000 |
| JP | 2001508555 | 6/2001 |
| JP | 2001247466 | 9/2001 |
| JP | 2002025690 | 1/2002 |
| JP | 2002243190 | 8/2002 |
| JP | 3343443 B2 | 11/2002 |
| JP | 2003248200 | 9/2003 |
| JP | 2003311762 | 11/2003 |
| JP | 2004085655 | 3/2004 |
| JP | 2004537348 | 12/2004 |
| JP | 2005513173 | 5/2005 |
| JP | 6312013 B2 | 4/2018 |
| KR | 19900008008 B1 | 10/1990 |
| TW | 559588 B | 11/2003 |

(56) References Cited

FOREIGN PATENT DOCUMENTS

| | | |
|---|---|---|
| TW | 567215 | 12/2003 |
| TW | 585882 B | 5/2004 |
| TW | 588078 B | 5/2004 |
| TW | 592738 | 6/2004 |
| TW | 200424248 A | 11/2004 |
| WO | 93/09154 A1 | 5/1993 |
| WO | 1994004028 A1 | 3/1994 |
| WO | 1994009794 A1 | 5/1994 |
| WO | 1994015648 A1 | 7/1994 |
| WO | 1994016743 A1 | 8/1994 |
| WO | 1994021698 A1 | 9/1994 |
| WO | 1995020969 A1 | 8/1995 |
| WO | 96/31792 A1 | 10/1996 |
| WO | 1997049740 A1 | 12/1997 |
| WO | 1998011875 A1 | 3/1998 |
| WO | 1998030248 A2 | 7/1998 |
| WO | 2000002937 A1 | 1/2000 |
| WO | 2000019981 A1 | 4/2000 |
| WO | 2000037048 A1 | 6/2000 |
| WO | 2000037541 A1 | 6/2000 |
| WO | 2000059970 A1 | 10/2000 |
| WO | 2001009211 A1 | 2/2001 |
| WO | 2001071392 A1 | 9/2001 |
| WO | 2001082984 A2 | 11/2001 |
| WO | 2002092143 A1 | 11/2002 |
| WO | 2003/022322 A2 | 3/2003 |
| WO | 2003022321 A2 | 3/2003 |
| WO | 2003057270 A1 | 7/2003 |
| WO | 2004010204 A1 | 1/2004 |
| WO | 2004028536 A1 | 4/2004 |
| WO | 2006012000 A1 | 2/2006 |
| WO | 2006088758 A2 | 8/2006 |

OTHER PUBLICATIONS

Barabas, (1989) "N-Vinyl Amide Polymers", Encyclopedia of Polymer Science and Engineering, 2nd Edition, vol. 17, 198-257, John Wiley & Sons, Inc, New York, 63 pages.

Brewitt et al, Rewetting of contact lenses: Clinical data on efficacy and necessity, Contactologia, International Medical Contact Lens Journal, German Edition, vol. 16, No. 3, 3rd Quarter 1994 (III), pp. 87-142, 10 pages.

Chalyovska et al, Development of a Medium for Improving the Tolerance of Contact Lenses, Their Maintenance and Storage, Annals of Sofia University named after Kliment Ohridski College of Chemistry, vol. 74, 1984 Translation, 4 pages.

Comelli et al, Estimation of Molecular Weight Distribution of Poly(Vinylpyrrolidone) from Diaphragm-Cell Diffusion Measurements, Polymer Engineering & Science, vol. 20, No. 5, Mar. 1980, 6 pages.

Crivello, et al, Photoinitiators for Free Radical Cationic & Anionic Photopolymerisation, 2nd Edition, vol. III, pp. 275-298, John Wiley and Sons, New York, 1998.

Das et al, Evaluation of Glutaraldehyde and Povidone Iodine for Sterilization of Wide-Field Contact Vitrectomy Lenses, Ophthalmic Surgery and Lasers, vol. 32, No. 4, pp. 300-304, Jul./Aug. 2001.

Das et al, Rapid Sterilization of Wide Field Contact Lens Used in Vitreo-Retinal Surgery, Investigative Ophthalmology & Visual Science vol. 40, No. 4, Mar. 15, 1999, 1 page.

De La Iglesia et al, Soft Contact Lens Studies in Rabbit Eyes, Toxicology and Applied Pharmacology 29(1):96-97, 1974, 1 page.

Dexter, Interactions of Anionic Surfactants and Polymers Used as Spray Tank Adjuvants, 16th Volume, ASTM STP (1312):77-92, 1996.

Dimitrova et al, Formulation of New Products—Purolens and Filmolens, for Maintenance of Hard Contact Lenses, Farmats, XXXIII, vol. 5, 1983, 5 pages.

Federov et al, A Liquid-Chromatographic Study of the Molecular Mass and Composition Heterogeneity of Random Copolymers of N-Vinylpyrrolidone and 2-Methyl-5-vinylpyridine, Polymer Science Series A, vol. 36, No. 9, pp. 1291-1294, 1994.

Fleig et al, The Effect of Column Geometry on Separation Effectiveness of Agarose for Poly(Vinyl Pyrrolidone), Chemical Engineering Communications, vol. 13, pp. 219-229, 1982.

Hoefle, Contact Lens Materials: Past, Present, and Future, American Academy of Ophthalmology and Otolaryngology, vol. 78, No. 3, pp. OP386-390, May/Jun. 1974.

Hornbrook et al, Soft Flexible Contact Lenses, The Medical Journal of Australia, pp. 649-653, Sep. 29, 1973.

ISO 9913-1: 1996: Optics and optical instruments—Contact Lenses—Part 1: Determination of oxygen permeability and transmissibility by the FATT method, 16 pages.

Jiang et al, Characterization of water-soluble polymers by flow FFF-MALS, American Laboratory, pp. 98-108, Feb. 2000, 11 pages.

Kunzler, "Silicone Hydrogels For Contact Lens Application", Trends in Polymer Science, Feb. 1996, pp. 52-59, vol. 4, No. 2, Elsevier Trends Journals, Cambridge, UK.

Leonard-Stibbe et al, The Cationic Polymerisation of N-Vinyl-2-pyrrolidone Initiated Electrochemically by Anodic Polarisation on a Pt Surface, Journal of Polymer Science: Part A: Polymer Chemistry, vol. 32, pp. 1551-1555, (1994), 5 pages.

Manning, The Application of Centrifugation to Polymer Fractionation, Dissertation Abstracts International. Section B, The Sciences and Engineering 32(9):5164-5, 1972, 3 pages.

McCarey et al, Refractive keratoplasty with intrastromal hydrogel lenticular implants, Investigative Ophthalmology & Visual Science 21 (1 Part 1):107-115, Jul. 1981.

PCT International Preliminary Report on Patentability dated Aug. 14, 2007, or PCT Int'l. Appln. No. PCT/US2006/004877, 8 pages.

PCT International Search Report dated Jul. 15, 2011 PCT Int'l Appln No. PCT/US2011/032413, 5 pages.

PCT International Search Report, dated Feb. 9, 2007, for PCT Int'l. Appln. No. PCT/US2006/004877, 4 pages.

Pilyugina et al, In Vitro Epithelialization of a Synthetic Polymer for Generation of Corneal Onlay/keratoprosthesis, Investigative Ophthalmology & Visual Science 44: E-Abstract, pp. 1344-B240, May 2003, 2 pages.

Princz et al., Release of Wetting Agents from Nelfilcon Contact Lenses, Investigative Ophthalmology & Visual Science, Association for Research in Vision, vol. 46, No. Suppl S, May 2005, p. 907-B881, 1 page.

Refojo, Contact Lenses and Pharmaceutical Solutions for Their Care, Storage and Disinfection, Schepens Eye Research Institute and Department of Ophthalmology, Harvard Medical School, Boston, MA, An. Real Acad, Farm., 1996, 62: 401-420.

Riedhammer et al, Effects of long-term heat disinfection on Soflens (polymacon) contact lenses, Journal of the American Optometric Association, vol. 51, No. 3, pp. 287-289, Mar. 1980.

Riedhammer, Colorimetric Determination of Poly(N-Vinyl-2-Pyrrolidone) in Contact Lens Solutions, Journal of the Association of Official Analytical Chemists, vol. 62, No. 1, pp. 52-55, 1979.

Rucker et al, A Safety Test for Contact Lens Wetting Solutions, Annals of Ophthalmology, pp. 1000-1006, Nov. 1972.

Special 510 (k) Summary of Safety and Efficacy for VISTAKON®, dated Nov. 1, 2006, 9 pages.

Udupa et al, Studies on Physicochemical Properties of Viscosity Building Agents Used in Contact Lens Solutions, The Indian Journal of Hospital Pharmacy, vol. 13, pp. 184-189, Nov.- Dec. 1976, 7 pages.

Ye et al, Formation of Monodisperse Polyacrylamide Particles by Radiation-Induced Dispersion Polymerization. I. Synthesis and Polymerization Kinetics, Journal of Applied Polymer Science, vol. 86, pp. 2567-2573, (2002).

Extended European Search Report Received for European Patent Application No. 22202280.8, dated Mar. 7, 2023, 10 pages.

\* cited by examiner

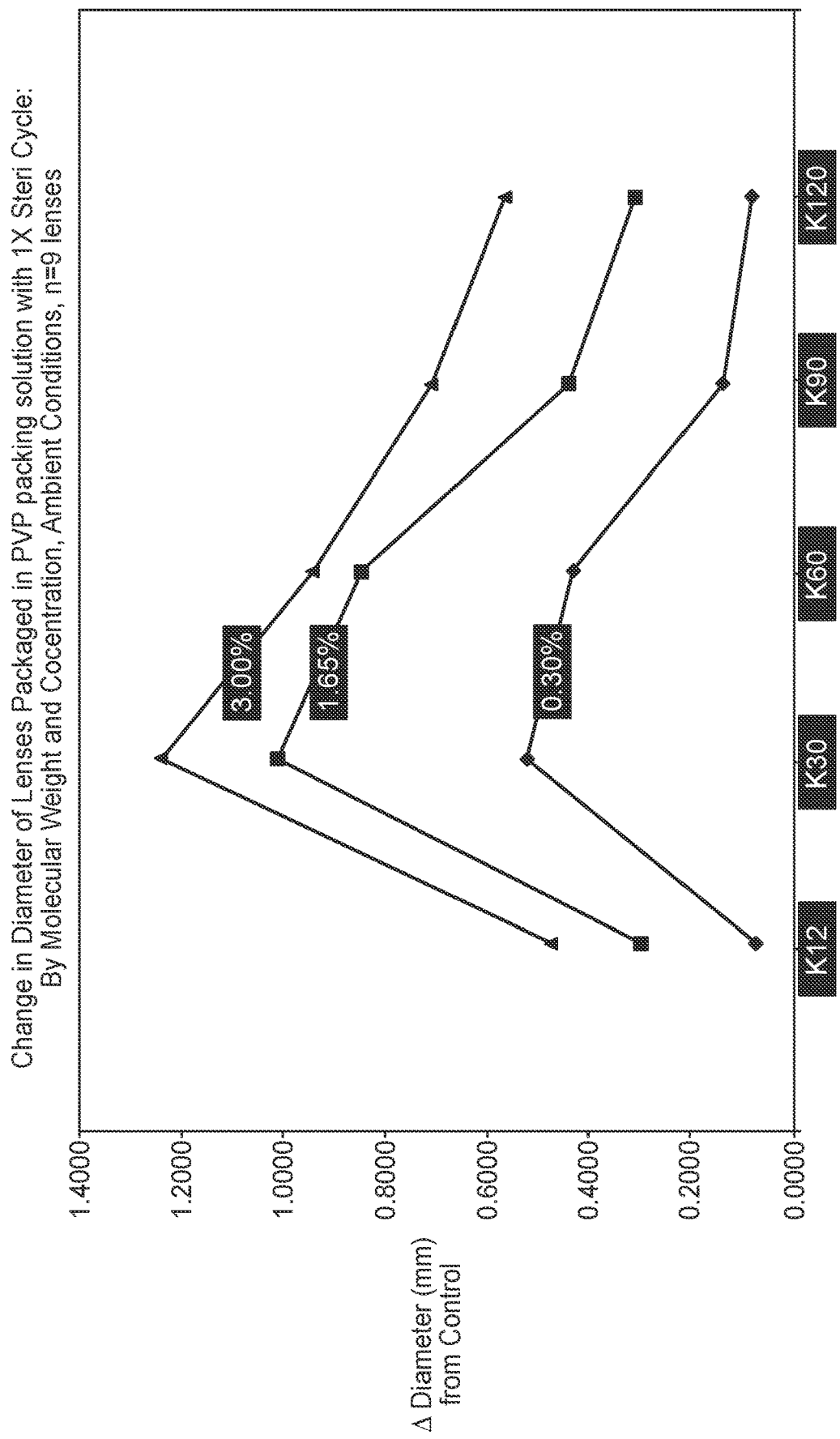

COMFORTABLE OPHTHALMIC DEVICE AND METHODS OF ITS PRODUCTION

RELATED APPLICATIONS

This application is a continuation of U.S. Ser. No. 16/293,819, filed Mar. 6, 2019, now U.S. patent Ser. No. 11/150,383, issued Oct. 19, 2021, which is a continuation of U.S. Ser. No. 15/175,526, filed Jun. 7, 2016, now U.S. Pat. No. 10,267,952, issued Apr. 23, 2019, which is a divisional of U.S. Ser. No. 14/196,006, filed Mar. 4, 2014, now U.S. Pat. No. 9,395,559, issued Jul. 19, 2016, which is a divisional of U.S. Ser. No. 12/896,930, filed Oct. 4, 2010, now U.S. Pat. No. 8,696,115, issued Apr. 15, 2014, which is a continuation of U.S. Ser. No. 11/351,907, filed Feb. 10, 2006, now U.S. Pat. No. 7,841,716 issued Nov. 30, 2010, which is a non-provisional filing of two provisional applications, U.S. Ser. No. 60/652,809, filed on Feb. 14, 2005 and U.S. Ser. No. 60/695,783 filed on Jun. 30, 2005.

FIELD OF THE INVENTION

This invention relates to comfortable ophthalmic devices and methods of producing such devices.

BACKGROUND

Contact lenses have been used commercially to improve vision since the 1950s. The first contact lenses were made of hard materials. Although these lenses are currently used, they are not suitable for all patients due to their poor initial comfort. Later developments in the field gave rise to soft contact lenses, based upon hydrogels, which are extremely popular today. These lenses have higher oxygen permeabilities and such are often more comfortable to wear than contact lenses made of hard materials. However, these new lenses are not without problems.

Contact lenses can be worn by many users for 8 hours to several days in a row without any adverse reactions such as redness, soreness, mucin buildup and symptoms of contact lens related dry eye. However, some users begin to develop these symptoms after only a few hours of use. Many of those contact lens wearers use rewetting solutions to alleviate discomfort associated with these adverse reactions with some success. However the use of these solutions require that users carry extra solutions and this can be inconvenient. For these users a more comfortable contact lens that does not require the use of rewetting solutions would be useful. Therefore there is a need for such contact lenses and methods of making such contact lenses. It is this need that is met by the following invention.

BRIEF DESCRIPTION OF THE DRAWINGS

FIG. 1 Plot of the change in diameter of treated lenses versus control.

DETAILED DESCRIPTION OF THE INVENTION

This invention includes a method of producing ophthalmic lenses comprising, consisting essentially of, or consisting of, treating a polymerized ophthalmic lens with a wetting agent, provided that the ophthalmic lens formulation does not comprise said wetting agent prior to its polymerization.

As used herein, "ophthalmic lens" refers to a device that resides in or on the eye. These devices can provide optical correction or may be cosmetic. Ophthalmic lenses include but are not limited to soft contact lenses, intraocular lenses, overlay lenses, ocular inserts, and optical inserts. The preferred lenses of the invention are soft contact lenses made from silicone elastomers or hydrogels, which include but are not limited to silicone hydrogels, and fluorohydrogels. Soft contact lens formulations are disclosed in U.S. Pat. No. 5,710,302, WO 9421698, EP 406161, JP 2000016905, U.S. Pat. Nos. 5,998,498, 6,087,415, 5,760,100, 5,776,999, 5,789,461, 5,849,811, and 5,965,631. The foregoing references are hereby incorporated by reference in their entirety. The particularly preferred ophthalmic lenses of the inventions are known by the United States Approved Names of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, genfilcon A, govafilcon A, hefilcon A, hefilcon B, hefilcon D, hilafilcon A, hilafilcon B, hioxifilcon B, hioxifilcon C, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, silafilcon A, siloxyfilcon A, tefilcon A, tetrafilcon A, trifilcon A, and xylofilcon A. More particularly preferred ophthalmic lenses of the invention are genfilcon A, lenefilcon A, comfilcon, lotrafilcon A, lotraifilcon B, and balafilcon A. The most preferred lenses include etafilcon A, nelfilcon A, hilafilcon, and polymacon.

The term "formulation" refers to the un-polymerized mixture of components used to prepare ophthalmic lenses. These components include but are not limited to monomers, pre-polymers, diluents, catalysts, initiators tints, UV blockers, antibacterial agents, polymerization inhibitors, and the like. These formulations can be polymerized, by thermal, chemical, and light initiated curing techniques described in the foregoing references as well as other references in the ophthalmic lens field. As used herein, the terms "polymerized" or "polymerization" refers to these processes. The preferred methods of polymerization are the light initiated techniques disclosed in U.S. Pat. No. 6,822,016 which is hereby incorporated by reference in its entirety.

As used herein the term "treating" refers to physical methods of contacting the wetting agents and the ophthalmic lens. These methods exclude placing a drop of a solution containing wetting agent into the eye of an ophthalmic lens wearer or placing a drop of such a solution onto an ophthalmic lens prior to insertion of that lens into the eye of a user. Preferably treating refers to physical methods of contacting the wetting agents with the ophthalmic lenses prior to selling or otherwise delivering the ophthalmic lenses to a patient. The ophthalmic lenses may be treated with the wetting agent anytime after they are polymerized. It is preferred that the polymerized ophthalmic lenses be treated with wetting agents at temperature of greater than about 50° C. For example in some processes to manufacture contact lenses, an un-polymerized, or partially polymerized formulation is placed between two mold halves, spincasted, or static casted and polymerized. See, U.S. Pat. Nos. 4,495,313; 4,680,336; 4,889,664, 3,408.429; 3,660,545; 4,113,224; and 4,197,266, all of which are incorporated by reference in their entirety. In the case of hydrogels, the ophthalmic lens formulation is a hardened disc that is subjected to a number of different processing steps including treating the polymerized ophthalmic lens with liquids (such as water, inorganic salts, or organic solutions) to swell, or otherwise equilibrate this polymerized ophthalmic lens prior to enclosing the polymerized ophthalmic lens in its final packaging. Polymerized ophthalmic lenses that have not been swelled or otherwise equilibrated are known as un-hydrated polymerized ophthalmic lenses. The addition of the wetting agent to any of the liquids of this "swelling or "equilibrating" step at room temperature or below is considered "treating" the lenses with wetting agents as contemplated by this invention. In addition, the polymerized un-hydrated ophthalmic lenses may be heated above room temperature with the wetting agent during swelling or equilibrating steps. The preferred temperature range is from about 50° C. for about 15 minutes to about sterilization conditions as described below, more preferably from about 50° C. to about 85° C. for about 5 minutes.

Yet another method of treating is physically contacting polymerized ophthalmic lens (either hydrated or un-hydrated) with a wetting agent at between about room temperature and about 85° C. for about 1 minute to about 72 hours, preferably about 24 to about 72 hours, followed by physically contacting the polymerized ophthalmic lens with a wetting agent at between about 85° C. and 150° C. for about 15 minutes to about one hour.

Many ophthalmic lenses are packaged in individual blister packages, and sealed prior to dispensing the lenses to users. As used herein, these polymerized lenses are referred to as "hydrated polymerized ophthalmic lenses". Examples of blister packages and sterilization techniques are disclosed in the following references which are hereby incorporated by reference in their entirety, U.S. Pat. Nos. D435,966 S; 4,691,820; 5,467,868; 5,704,468; 5,823,327; 6,050,398, 5,696,686; 6,018,931; 5,577,367; and 5,488,815. This portion of the manufacturing process presents another method of treating the ophthalmic lenses with wetting agents, namely adding wetting agents to packaging solution prior to sealing the package, and subsequently sterilizing the package. This is the preferred method of treating ophthalmic lenses with wetting agents.

Sterilization can take place at different temperatures and periods of time. The preferred sterilization conditions range from about 100° C. for about 8 hours to about 150° C. for about 0.5 minute. More preferred sterilization conditions range from about 115° C. for about 2.5 hours to about 130° C. for about 5.0 minutes. The most preferred sterilization conditions are about 124° C. for about 30 minutes.

The "packaging solutions" that are used in methods of this invention may be water-based solutions. Typical packaging solutions include, without limitation, saline solutions, other buffered solutions, and deionized water. The preferred aqueous solution is deioinized water or saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2, 2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the packaging solution is a borate buffered or phosphate buffered saline solution or deionized water. The particularly preferred packaging solution contains about 1,850 ppm to about 18,500 ppm sodium borate, most particularly preferred about 3,700 ppm of sodium borate.

As used here, the term "wetting agent" refers polymers having a number average molecular weight of about at least 500, that impart a moist feeling when added to the eyes of contact lens wearers. Examples of preferred wetting agents include but are not limited to poly(meth)acrylamides [i.e. poly N,N-dimethylacrylamide), poly (N-methylacrylamide) poly (acrylamide), poly(N-2-hydroxyethylmethacrylamide), and poly(glucosamineacrylamide)], poly(itaconic acid), hyaluronic acid, xanthan gum, gum Arabic (acacia), starch, polymers of hydroxylalkyl(meth)acrylates [i.e. poly(2-hydroxyethylmethacrylate), poly(2,3-dihydroxypropylmethacrylate, and poly(2-hydroxyethylacrylate)], and polyvinylpyrrolidone.

Additional preferred wetting agents include but are not limited to co-polymers and graft co-polymers of the aforementioned preferred wetting agents, such co-polymers and graft co-polymers include repeating units of hydrophilic or hydrophobic monomers, preferably in amounts of about less than ten percent by weight, more preferably less than about two percent. Such repeating units of hydrophilic or hydrophobic monomers include but are not limited to alkenes, styrenes, cyclic N-vinyl amides, acrylamides, hydroxyalkyl (meth) acrylates, alkyl (meth) acrylates, siloxane substituted acrylates, and siloxane substituted methacrylates. Specific examples of hydrophobic or hydrophilic monomers which may be used to form the above co-polymers and graft co-polymers include but are not limited to ethylene, styrene, N-vinylpyrrolidone, N,N-dimethylacrylamide, 2-hydroxyethylmethyacrylate, methyl methacrylate and butyl methacrylate, methacryloxypropyl tristrimethylsiloxysilane and the like. The preferred repeating units of hydrophilic or hydrophobic monomers are N-vinylpyrrolidone, N,N-dimethylacrylamide, 2-hydroxyethylmethacrylate, methyl methacrylate, and mixtures thereof. Further examples of wetting agents include but are not limited to polymers with carbon backbones and pendant polyethylene glycol chains [i.e. polymers of polyethylene glycol monoomethacrylate] copolymers of ethylene glycol [copolymers with 1,2,propyleneglycol, 1,3-propylene glycol, methyleneglycol, and tetramethylene glycol]. The preferred wetting agents are polyvinylpyrrolidone, graft co-polymers and co-polymers of polyvinylpyrrolidone, the particularly preferred wetting agent is polyvinylpyrrolidone. Polyvinylpyrrolidone ("PVP") is the polymerization product of N-vinylpyrrolidone. PVP is available in a variety of molecular weights from about 500 to about 6,000,000 Daltons. These molecular weights can be expressed in term of K-values, based on kinematic viscosity measurements as described in Encyclopedia of Polymer Science and Engineering, John Wiley & Sons Inc, and will be expressed in these numbers throughout this application. The use of PVP having the following K-values from about K-30 to about K-120 is contemplated by this invention. The more preferred K-values are about K-60 to about K-100, most preferably about K-80 to about K-100. For the treatment of etafilcon A lenses, the particularly preferred K-value of PVP is about K-80 to about K-95, more preferably about K-85 to about K-95, most preferably about K-90.

The wetting agents can be added to the packaging solution at a variety of different concentrations such as about 100 ppm to about 150,000 ppm. For example if the wetting agents are added to packaging solutions containing un-hydrated polymerized ophthalmic lenses, the wetting agents are preferably present at a concentration of about 30,000 ppm to about 150,000 ppm. If the wetting agents are added to packaging solutions containing hydrated polymerized ophthalmic lenses, the wetting agents are preferably present at a concentration of about 100 ppm, to about 3000 ppm, more preferably about 200 ppm to about 1000 ppm, most preferably less than about 500 ppm. For example when etafilcon A lenses are used in this invention and the wetting agent is K-90 PVP, the preferred packaging solution concentration of PVP K-90 is about 250 ppm to about 2,500 ppm, more preferably about 300 to about 500 ppm, most preferably about 350 to about 440 ppm.

When etafilcon A contact lenses are heated with K-90 PVP at a temperature greater than about 120° C. for about 30 minutes at a concentration of about 400 to about 500 ppm, the treated lenses are more comfortable to users than untreated lenses. Further, this particular molecular weight and concentration of PVP does not distort or shift the diameter of the lenses during the treatment cycle or distort the users vision. While not wishing to be bound by any particular mechanism of incorporation, it is known that K-90 PVP is incorporated into the matrix of the lens after it is treated with K-90 PVP. In an etafilcon A contact lens, the preferred amount of incorporated K-90 PVP is about 0.01 mg to about 1.0 mg, more preferred about 0.10 mg to about 0.30 mg, most particularly preferred about 0.10 mg to about 0.20 mg. Lenses that have been treated in this manner are worn by users for up to 12 hours still maintain the incorporated PVP.

Further the invention includes an ocular device comprising, consisting essentially of, or consisting of a polymerized ophthalmic lens wherein said polymerized ophthalmic lens is treated with a wetting agent, provided that the ophthalmic lens formulation does not comprise said wetting agent prior to its polymerization. The terms "ophthalmic lens," "wetting agent," "polymerized," and "formulation" all have their aforementioned meanings and preferred ranges. The term "treated" has the equivalent meaning and preferred ranges as the term treating.

Still further the invention includes an ocular device prepared by treating a polymerized ophthalmic lens with a wetting agent, provided that the ophthalmic lens formulation does not comprise said wetting agent prior to its polymerization. The terms "ophthalmic lens," "wetting agent," "polymerized," "treated" and "formulation" all have their aforementioned meanings and preferred ranges.

The application of the invention is described in further detail by use of the following examples. These examples are not meant to limit the invention, only to illustrate its use. Other modifications that are considered to be within the scope of the invention, and will be apparent to those of the appropriate skill level in view of the foregoing text and following examples.

EXAMPLES

Example 1

Cured etafilcon A contact lenses (sold as 1-Day Acuvue® brand contact lenses by Johnson & Johnson Vision Care, Inc.) were equilibrated in deionized water, and packaged in solutions containing PVP in borate buffered saline solution ((1000 mL, sodium chloride 3.55 g, sodium borate 1.85 g, boric acid 9.26 g, and ethylenediamine tetraacetic acid 0.1 g: 5 rinses over 24 hours, 950±µL), sealed with a foil lid stock, and sterilized (121° C., 30 minutes). Before the addition of PVP each solution contained water, 1000 mL, sodium chloride 3.55 g, sodium borate 1.85 g, boric acid, 9.26 g, and ethylenediamine tetraacetic acid 0.1 g. A variety of different weights and concentrations of PVP were used as shown in Table 1, below The amount of PVP that is incorporated into each lens is determined by removing the lenses from the packaging solution and extracting them with a mixture 1:1 mixture of N,N-dimethylforamide, (DMF) and deionized water (Dl). The extracts are evaluated by high performance liquid chromatography (HPLC). Three lenses were used for each evaluation. The results and their standard deviation are presented in Table 1.

TABLE 1

| Sample # | Type of PVP | Conc. (ppm) | mg of PVP in lens |
|---|---|---|---|
| Control | None | None | none |
| 1 | K-12 | 3000 | 0.24 (0.01) |
| 2 | K-12 | 20,000 | 1.02 (0.01) |
| 3 | K-30 | 1500 | 1.39 (0.05) |
| 4 | K-30 | 2000 | 1.50 (0.01) |
| 5 | K-60 | 1000 | 0.56 (0.00) |
| 6 | K-60 | 1500 | 0.85 (0.02) |
| 7 | K-60 | 2500 | 1.02 (0.03) |
| 8 | K-90 | 250 | 0.10 (0.00) |
| 9 | K-90 | 500 | 0.14 (0.00) |
| 10 | K-90 | 1000 | 0.2 (0.01) |
| 11 | K-90 | 2500 | 0.25 (0.02) |
| 12 | K-120 | 500 | 0.07 (0.00) |

Example 2

Samples of treated etafilcon A lenses were prepared via the treatment and sterilization methods of Example 1 from K-12, K-30, K-60, K-90, and K-120 PVP at concentrations of 0.30%, 1.65%, and 3.00%. After sterilization, the diameter of the lenses was, compared to an untreated lens and evaluated to determine if the process changed those diameters. The results, FIG. 1, plot the change in diameter vs the type of PVP at a particular concentration. This data shows that K-12, K-90, and K-120 have a minimal effect on the diameter of the lenses.

Example 3

Several etafilcon A lenses were treated with K-90 PVP at a concentration of 500 ppm and sterilized according to the methods of Example 1. The lenses were stored in their packages for approximately 28 days at room temperature and were then measured for diameter, base curve, sphere power, and center thickness. Thereafter, lenses were heated at 55° C. for one month. The diameter, base curve, sphere power, and center thickness of the lenses was measured and the results were evaluated against an untreated lens and data is presented in Table 2. This data illustrates that the parameters of lenses treated with K-90 PVP are not significantly affected by time at elevated temperature.

TABLE 2

| | Baseline | Change from Baseline of Sample after one month storage at 55° C. |
|---|---|---|
| Diameter (mm) | 14.37 (0.02) | 0.02 |
| Base curve (mm) | 8.90 (0.03) | −0.01 |
| Power (diopter) | −0.75 (0.05) | 0.00 |
| Center Thickness (mm) | 0.127 (0.005) | 0.002 |

Example 4

Etafilcon-A lenses treated with PVP K-90 at a concentration of 440 ppm and sterilized (124° C., approximately 18 minutes) were sampled from manufacturing lines and measured for diameter, base curve, sphere power, and center thickness and compared to similar measurements made on untreated 1-Day Acuvue® brand lenses. The data presented in Table 3 illustrates that K-90 PVP does not significantly affect these parameters.

TABLE 3

|  | Treated | Untreated |
| --- | --- | --- |
| Diameter (mm) | 14.24 (0.04) | 14.18 (0.04) |
| Base curve (mm) | 8.94 (0.03) | 8.94 (0.04) |
| Sphere Power Deviation from Target (diopter) | −0.01 (0.04) | −0.02 (0.04) |

TABLE 3-continued

|  | Treated | Untreated |
| --- | --- | --- |
| Center Thickness Deviation from Target (mm) | 0.000 (0.004) | 0.002 (0.005) |

Example 5

Etafilcon A lenses were prepared according to Example 1 at the concentrations of Table 1. The treated lenses were clinically evaluated in a double-masked studies of between 9 and 50 patients. The patients wore the lenses in both eyes for 3-4 days with overnight removal and daily replacement, and wore untreated 1-Day Acuvue® brand contact lenses for 3-4 days with overnight removal and daily replacement as a control. Patients were not allowed to use rewetting drops with either type of lens. Patients were asked to rate the lens using a questionnaire. All patients were asked a series of questions relating to overall preference, comfort preference, end of day preference, and dryness. In their answers they were asked to distinguish if they preferred the treated lens, the 1-Day control lens, both lenses or neither lens. The results are shown in Tables 4 and 5. The numbers in the columns represent the percentage of patients that positively responded to each of the four options. The "n" number represents the number of patients for a particular sample type. "DNT" means did not test and n/a means non applicable. The numbers illustrate that lenses treated with K-90 PVP at a concentration of about 500 ppm have good clinical comfort on the eye. The sample # refers to the sample numbers in Table 1.

TABLE 4

| | | Overall Preference, % | | | | Comfort Preference, % | | | |
| --- | --- | --- | --- | --- | --- | --- | --- | --- | --- |
| Sample # | n | PVP treated | 1-Day | Both | Neither | PVP treated | 1-Day | Both | Neither |
| 1 | 9 | 67 | 22 | 11 | 0 | 67 | 22 | 11 | 0 |
| 2 | 37 | 27 | 49 | 22 | 3 | 30 | 46 | 19 | 5 |
| 3 | 41 | 34 | 49 | 15 | 2 | 27 | 56 | 12 | 5 |
| 4 | 10 | 30 | 20 | 50 | 0 | 30 | 40 | 30 | 0 |
| 5 | 41 | 27 | 61 | 10 | 2 | 22 | 49 | 29 | 0 |
| 6 | 42 | 33 | 33 | 33 | 0 | 33 | 29 | 38 | 0 |
| 7 | 37 | 51 | 27 | 19 | 3 | 49 | 11 | 38 | 3 |
| 8 | 41 | 27 | 37 | 32 | 5 | 24 | 34 | 37 | 5 |
| 9 | 48 | 33 | 27 | 40 | 0 | 33 | 23 | 44 | 0 |
| 10 | 45 | 18 | 27 | 51 | 4 | 16 | 20 | 58 | 7 |

TABLE 5

| | | Dryness Preference % | | | | End of Day Preference %0 | | | |
| --- | --- | --- | --- | --- | --- | --- | --- | --- | --- |
| Sample # | n | PVP treated | 1-Day | Both | Neither | PVP treated | 1-Day | Both | Neither |
| 1 | 9 | 33 | 33 | 11 | 0 | 56 | 22 | 44 | 0 |
| 2 | 37 | 24 | 43 | 22 | 8 | 27 | 43 | 27 | 5 |
| 3 | 41 | 32 | 51 | 17 | 2 | 29 | 49 | 17 | 2 |
| 4 | 10 | 20 | 40 | 30 | 10 | 20 | 10 | 60 | 10 |
| 5 | 41 | 20 | 46 | 32 | 2 | 20 | 41 | 37 | 2 |
| 6 | 31 | 42 | 24 | 38 | 0 | 38 | 35 | 16 | 6 |
| 7 | 42 | 36 | 19 | 38 | 3 | 41 | 24 | 40 | 0 |
| 8 | 41 | 27 | 22 | 49 | 7 | 22 | 24 | 41 | 7 |
| 9 | 48 | 38 | 21 | 46 | 0 | 33 | 19 | 44 | 0 |
| 10 | 45 | 24 | 20 | 58 | 4 | 18 | 20 | 51 | 4 |

Example 6

An etafilcon A contact lens was treated with 500 ppm of K-90 PVP using the methods of Example 1. The treated lenses were briefly rinsed with phosphate buffered saline solution and rinsed lenses were placed in the well of a cell culture cluster container (Cellgrow XL) that mimics the dimensions of a human eye. See, Farris R L, Tear Analysis in Contact Lens Wears, *Tr. Am. Opth. Soc. Vol. LXXXIII*, 1985. Four hundred microliters of phosphate buffered saline solution ($KH_2PO_4$ 0.20 g/L, KCl 0.20 g/L, NaCl 8.0 g/L, $Na_2HPO_4$ [anhydrous] 1.15 g/L) was added to each container. The wells were covered and the container was stored in an oven at 35° C.

Three lenses were removed from the oven at various times and analyzed by HPLC to determine whether PVP was released into the phosphate buffered saline solution. The average results are presented in Table 6. The limit of quantification for PVP is 20 ppm. The test did not detect any PVP in the analyzed samples. This data shows that PVP is not released at levels greater than 20 ppm.

TABLE 6

| Time | PVP Released |
|---|---|
| 30 min. | <20 ppm |
| 1 hr. | <20 ppm |
| 2 hr. | <20 ppm |
| 4 hr. | <20 ppm |
| 8 hr. | <20 ppm |
| 16 hr. | <20 ppm |
| 24 hr | <20 ppm |

What is claimed is:

1. An ocular device prepared by treating a polymerized ophthalmic lens with a solution comprising about 200 to about 1000 ppm of a wetting agent selected from the group consisting of polyvinylpyrrolidone, graft co-polymers of polyvinylpyrrolidone, and co-polymers of polyvinylpyrrolidone, each having a K value between about K-60 to about K-120; and (b) heating to a temperature of at least about 50° C. to about 150° C., provided that the ophthalmic lens does not comprise said wetting agent prior to its polymerization.

2. The device of claim 1 wherein treating comprises heating the polymerized ophthalmic lens in a packaging solution to a temperature of greater than 80° C.

3. The device of claim 1 wherein the wetting agent is polyvinylpyrrolidone having a K-value of about K-60 to about K-90.

4. The device claim 1 wherein the ophthalmic lens is selected from the group consisting of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, genfilcon A, govafilcon A, hefilcon A, hefilcon B, hefilcon D, hilafilcon A, hilafilcon B, hioxifilcon B, hioxifilcon C, hixoifilcon A, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, silafilcon A, siloxyfilcon A, tefilcon A, tetrafilcon A, trifilcon A, and xylofilcon A.

5. The device of claim 1 wherein the ophthalmic lens is selected from the group consisting of genfilcon A, lenefilcon A, lotrafilcon A, lotrafilcon B, balifilcon A, comfilcon, etafilcon A, nelfilcon A, hilafilcon, and polymacon.

6. The device of claim 1 wherein the ophthalmic lens is etafilcon A.

* * * * *